United States Patent [19]

Grimm et al.

[11] 4,303,601
[45] Dec. 1, 1981

[54] VENTILATOR HUMIDIFIER

[75] Inventors: Daniel J. Grimm, McHenry, Ill.;
John M. Unger, Lake Geneva, Wis.;
Robert A. Virag, Cary, Ill.

[73] Assignee: Baxter Travenol Laboratories, Inc., Deerfield, Ill.

[21] Appl. No.: 135,555

[22] Filed: Mar. 31, 1980

[51] Int. Cl.³ .......................................... A61M 15/00
[52] U.S. Cl. .................................. 261/142; 261/104;
261/DIG. 65; 128/203.27; 128/204.13; 73/293
[58] Field of Search ...................... 261/66, 142, 95–97,
261/99, 102, 104, 107, DIG. 15, DIG. 65;
128/200.11, 203.26, 203.27, 204.13, 204.14,
204.17; 219/275; 137/392; 73/293, 327

[56] References Cited

U.S. PATENT DOCUMENTS

| | | | |
|---|---|---|---|
| 1,267,761 | 5/1918 | Goodfellow | 128/203.27 |
| 3,947,692 | 3/1976 | Payne | 73/293 |
| 4,028,444 | 6/1977 | Brown et al. | 261/142 |
| 4,110,419 | 8/1978 | Miller | 261/142 |
| 4,134,022 | 1/1979 | Jacobsen | 73/293 |
| 4,156,149 | 5/1979 | Vaccari | 73/293 |

OTHER PUBLICATIONS

Bulletin from Hi-G Electronics on Liquid Level Sensors, #EA 006, Dec. 1978, 580 Spring St. Windsor Locks, CT 06096.
Bulletin from Micro Switch on Optic Liquid Level Sensing, Oct.–1976, Freeport, 61032.

Primary Examiner—Gregory N. Clements
Attorney, Agent, or Firm—Paul C. Flattery; John A. Caruso; Garrettson Ellis

[57] ABSTRACT

A humidifier for gases, for example for medical administration, may be adapted for insertion into a well of a heater for warming liquid in the humidifier. A seamless metal can defines a cylindrical wall and a closed bottom end, containing wick means for absorbing water and presenting it in dispersed form to gases flowing through the can. Transparent probe means extend into the can and serve as a liquid level control for preferably automatically controlling the liquid level in the can to be maintained in the lower one third of the can.

8 Claims, 4 Drawing Figures

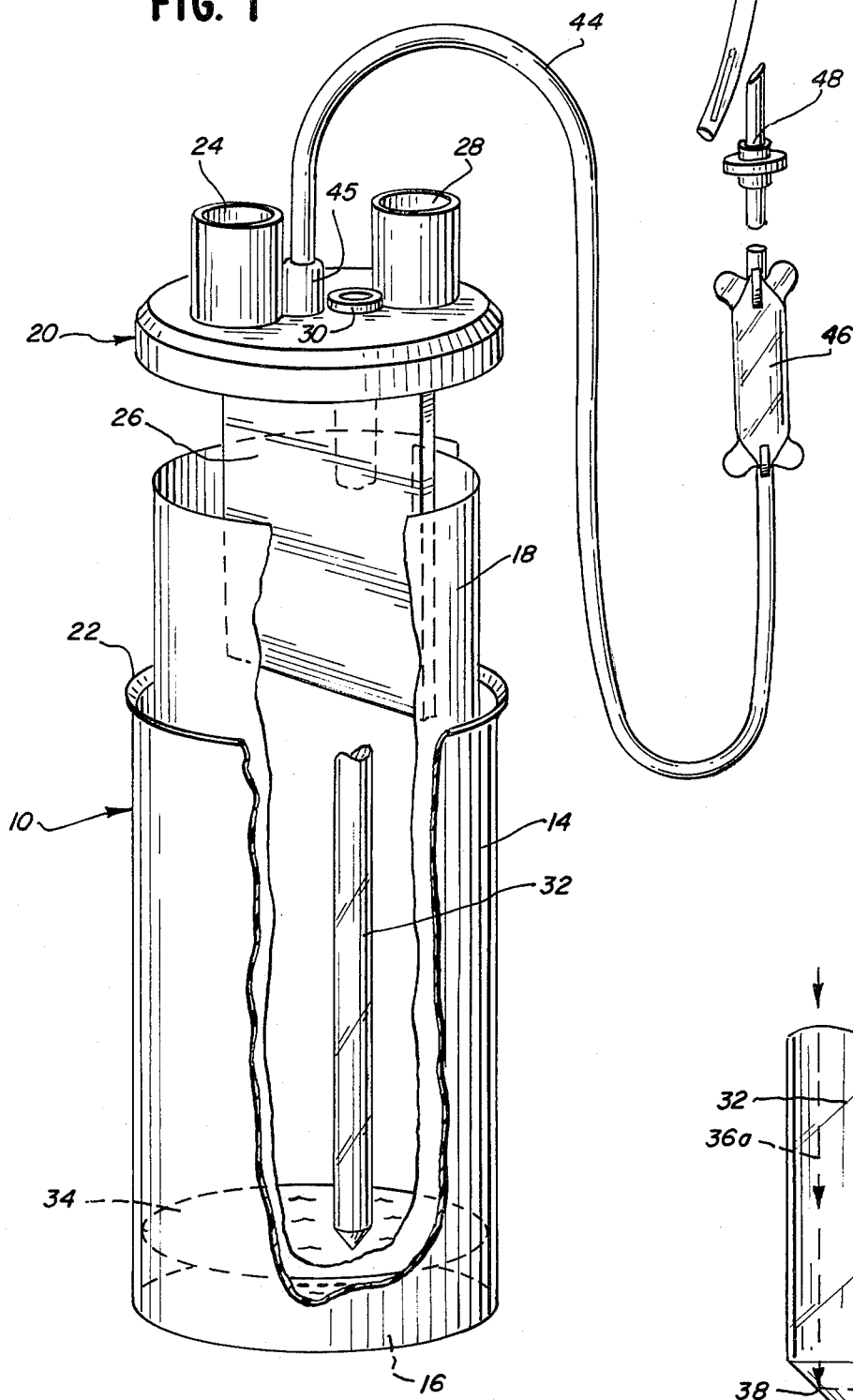

VENTILATOR HUMIDIFIER

BACKGROUND OF THE INVENTION

In U.S. Pat. No. 4,110,419 and U.K. published Patent Application No. 2,001,284A, humidifier members for oxygen gas or the like are disclosed utilizing cylindrical humidifier cartridges to function as a wick for transferring water vapor to gases passing through the device.

Such humidification devices in general are desirably used to humidify oxygen gas being administered to the patient, which is extremely dry in the form that it comes out of its pressurized container.

It is desirable to avoid the formation of liquid droplets in the gas in those circumstances where only humidification is desired, since the avoiding of droplets reduces transfer of bacteria which may be carried by the droplets, and also reduces the possibility of delivery of excessive amounts of water to the patient.

The humidifier of this invention is of the type in which water droplets are not generated, but only gases of increased humidity, (1) having accurate cotrolled temperature of the gas delivered to the patient, (2) low resistance to gas flow, which, in turn, allows usage of the invention of this application with demand-actuated ventilators, and (3) liquid level sensor means holding the liquid in the humidifier at a low level for optimum humidification characteristics of the system.

Also, the previously described humidifiers are of relatively expensive and cumbersome constructions, while, in accordance with this invention, a mass-produced, highly inexpensive, commercially available part can be utilized for substantial cost reduction in the manufacturing operation.

DESCRIPTION OF THE INVENTION

In accordance with this invention, a humidifier element for gases is provided, being adapted for insertion into the well of the heater for warming liquid in the humidifier, to improve the level of humidification of gases passing therethrough.

The humidifier element comprises a seamless, open-mouthed metal can defining cylindrical walls and a closed bottom end. For example, a commercial aluminum or steel beverage can may be used if desired, which, of course, is available at very low cost compared with specially designed structures.

Wick means, of preferably cylindrical shape, is positioned within the can for absorbing liquid water in the can, and presenting it in dispersed form to gases flowing through the can.

A closure seals the open mouth of the can, with the closure defining gas inlet and outlet aperture ports communicating with the can interior. The closure also defines a light access port, with transparent probe means communicating with the light access port and extending through the can to a least the remotest one-third of the can interior from the closure.

The transparent probe means defines an end surface adjacent the remotest third of the can interior which includes angled surfaces, positioned to permit light passing in the transparent probe toward the end surface, to be reflected again up the probe away from the end surface when the end surface is out of contact with liquid, and to be transmitted through the end surface when the probe is in contact with liquid.

As the result of this, photosensitive means can be positioned to detect reflected light in the probe. Flexible tubing can communicate with the can interior through the closure at one end, being adapted for communicating at its other end with a source of liquid in an elevated position over the can end closure. Valve means are then provided for controlling liquid flow through the tubing, with transducer means being provided for opening the valve means when the light sensing means detects reflected light in the transparent probe, indicative of a low liquid level in the can, and for closing the valve means when reflected light is not detected in the transparent probe.

The result of this is to provide a uniformly-maintained liquid level in the humidifier, with the liquid level being preferably maintained in the lower one third of the can interior, to provide a large wick area to enhance humidification of the gases flowing through the humidifier, so that the supply of liquid in the can remains no more than one third of the internal volume of the can.

In the drawings,

FIG. 1 is an exploded perspective view of the humidifier element of this invention.

FIG. 2 is an enlarged, fragmentary elevational view of the remote end of the light-transmitting probe.

Figure 3:
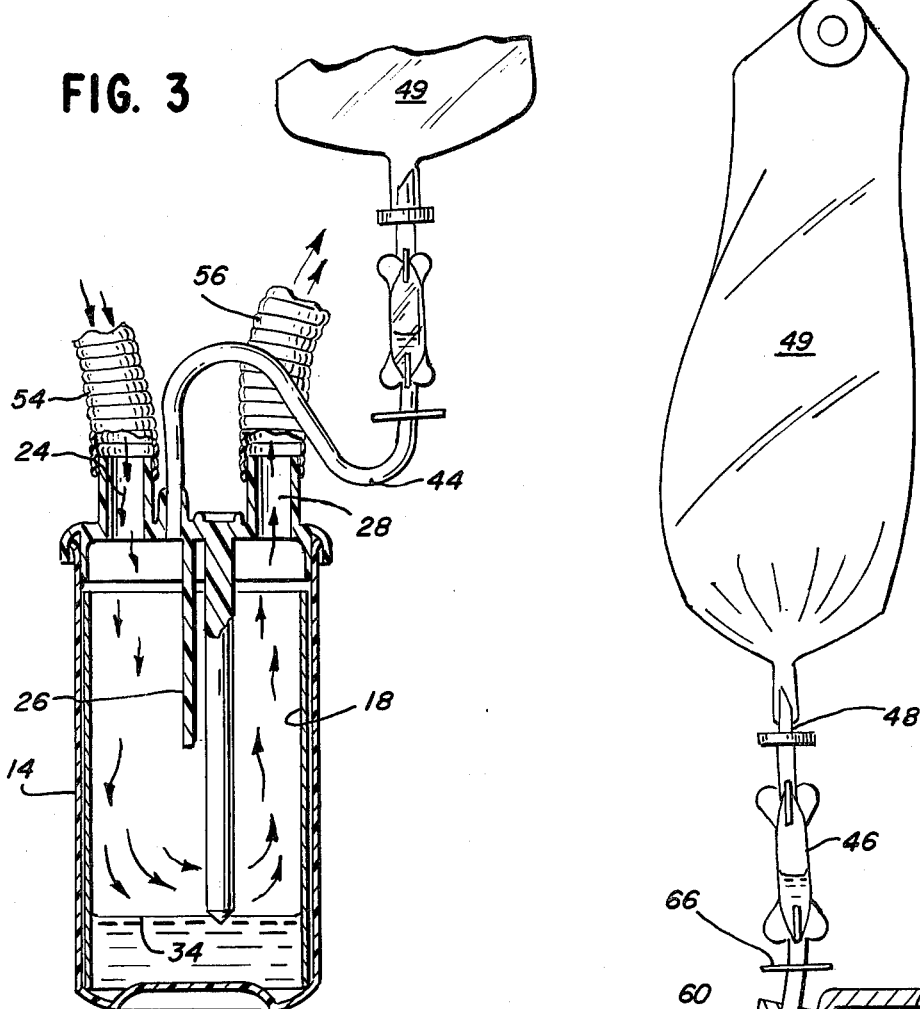
FIG. 3 is an elevational view taken partly in vertical section, showing the humidifier system of this invention in operation.

Referring to the drawings, humidifer element 10, which is adapted for insertion in the well of a heater assembly 12, comprises a seamless, open mouthed metal can 14 defining cylindrical walls and a closed bottom end 16. As stated previously, can 14 may simply be a commercial beverage can purchased from a can manufacturer at low cost for utilization in this invention.

Wick means 18 may be made from a sheet of material rolled up shown in FIG. 1 into a structure which is preferably generally cylindrical, the wick means being made of a porous paper material or the like. Accordingly, the wick means absorbs water in the bottom of can 14, and presents it in dispersed high surface area form to gases flowing through the can.

Closure 20 may be made of a single piece of molded plastic, and is adapted to fit in tight, sealing manner about the mouth 22 of can 14. Closure 20 defines a gas inlet port 24. Baffle 26 is provided to prevent shunting of non-humidified gas out of outlet aperture port 28, which is defined as shown by closure 20. Both inlet port 24 and outlet 28 are adapted for attachment to flexible gas flow tubing of conventional design for a patient breathing circuit or the like.

Closure 20 also defines light access port 30 through which may extend translucent probe means 32, which may be made of highly transparent acrylate plastic, polysulfone plastic, or the like. Probe means 32 extends through can 14 to at least the remotest third of the can interior from closure 20 to serve as a liquid level measuring means as described below, to keep the liquid level 34 in the lower third of the can. This exposes a large surface area of the wick member, which is preferably of essentially the same height as that of can 14, to take up the liquid and to expose a large surface area of wet wick 18 to the dry gases entering through inlet port 24, for improved humidification due to the large surface area, when compared with similar systems where the liquid level is maintained higher in the can.

Liquid level sensing probe 32 defines an end 33 which may be defined by a conical surface if desired, or any other surface which provides angled surfaces positioned to permit light 36a passing in the transparent probe toward end surface 33, to be reflected again up the probe in a returning beam of light 36b, after striking at two reflection points 38, 40, causing the light beam to make two 90° angle reflective turns. As can be seen, conical surface 42 preferably defines an angle of 45° to the axis of probe 32 and particularly the incoming light beam 36a, to achieve this result.

The light reflection as shown in FIG. 2 takes place when the end 33 of probe 32 is out of contact with liquid such as water.

When end 33 of the probe is in contact with liquid, the refractive conditions at conical surface 42 are changed because of the difference in the index of refraction of water with respect to air, so that light beam 36a is not refracted in the path indicated in FIG. 2, but instead passes through surface 42, continuing its downward path, so that there is no significant reflected light beam 36b. Accordingly, the presence or absence of contacting liquid at conical end surface 42 can be indicated by the presence or absence of a reflected light beam 36b.

Turning further to the structure of humidifier element 10, flexible tubing 44 is connected to a port 45 in closure 20 to supply water to the humidifier element 10. A standard drip chamber 46 is provided adjacent the free end of tubing 44, which terminates in a standard hollow piercing spike 48, for penetration into a conventional water supply container 49, for example, a bottle or bag of sterile water sold by Travenol Laboratories, Inc. of Deerfield, IL.

Figure 4:
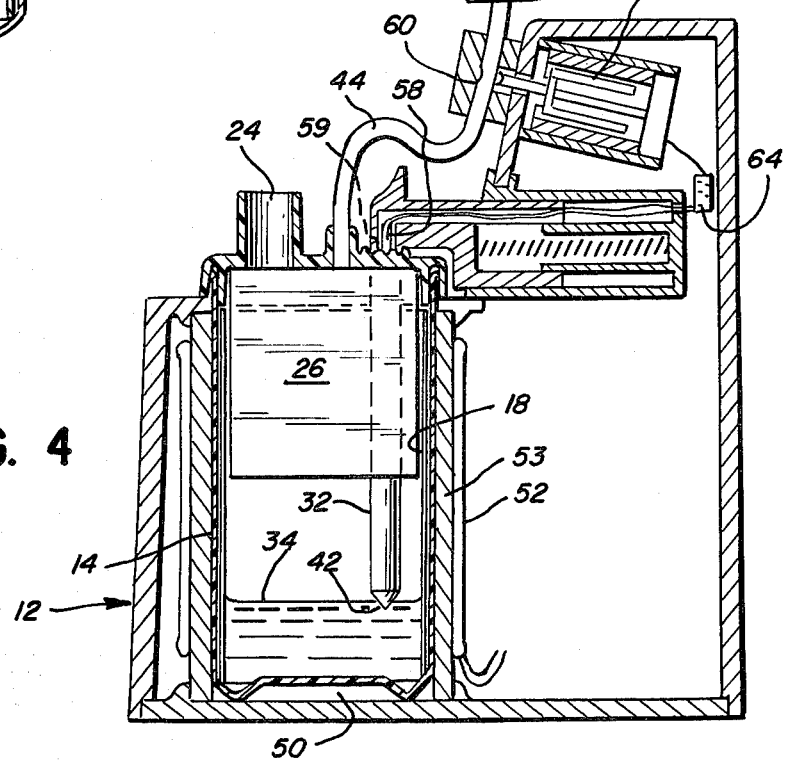
FIG. 4 is a cross-sectional view of the humidifier system rotated 90° about the vertical axis of FIG. 3.

Turning particularly to FIGS. 3 and 4, humidifier element 10 is shown installed in a heating well 50 of a heater apparatus 12. Heating coils 52 are shown, with humidifying element 10 being connected as in FIG. 3 to conventional gas tubing 54, 56.

Heater 52 may be a flexible strap heater mounted on aluminum heat exchange cylinder 52, which has an inner diameter sized to mate in heat exchange relationship with can 14. The exposed surface of the heat exchanger 53 may be coated with a plastic material such as polytetrafluoroethylene to prevent corrosion and abrasion.

Heater 52 may be controlled by temperature control circuitry that delivers power to the heater as required to maintain a pre-selected temperature at the patient. This circuitry can operate in a zero-voltage switching, time-proportioning mode to eliminate generation of electromagnetic interference. The desired temperature of the gas delivered to the patient may be controlled by means of a rotary potentiometer temperature adjustment, which may be placed on the control panel of the device.

Also, the temperature of the delivered gases may be monitored with a thermister temperature probe which may be inserted in an adaptor in the ventilator tubing near the patient. The electrical signal from this probe serves as an input to the temperature control circuitry, and to the circuitry associated, if desired, with the digital temperature display on the control panel of the device.

To guard against overfilling of can 14, a timer may be provided in the electric circuit to sense if tubing clamp 60 remains open in excess of the time required to fill a dry can 14 to its normal operating level. Since the time to fill a dry can 14 to its normal operating level from bag 49 may typically be 25 seconds. a tubing clamp remaining open in excess of this time indicates either a feed system malfunction or a depletion of the water supply. Thus, the timer closes clamp 60 after about 25 seconds.

Positioned at the top of probe 32 is photometer system 58, which comprises a light source, which may be a light emitting diode for sending a beam down the length of probe member 32. Infrared radiation (I.R.) may be used if desired. Also, an IR sensor 59 is present, similar to known design, to record the presence of a reflected light beam 36b.

If desired, IR sensor 59 and source 58 may operate in a synchronized pulse mode to eliminate the possibility of interference of ambient light sources, and may be mounted in an optically-shielded housing.

Tubing clamp 60 is provided to open and close tubing 44 in a manner actuated by solenoid 62, with tubing clamps 60 being normally in the closed position, to not permit liquid to pass through tubing 44 from container 49.

The IR sensor may be connected by an appropriate electronic circuit 64 to solenoid 62, to actuate solenoid 62 to open valve 60, permitting liquid flow through tubing 44 when reflected beam 36b is sensed. Liquid then flows into can 14 from bag 49, causing the water level 34 to rise until end surface 42 of probe 32 is covered. At this point, the reflected beam 36b terminates, which deactivates the IR sensor in photometric means 58, causing solenoid 62 to deactivate, which, in turn, closes valve 60, shutting off flow.

Accordingly, the liquid level 34 is maintained during operation of the humidifier element of this invention at a relatively constant level in the vicinity of the end surface 42 of probe member 32, for optimum humidification operation of the device of this invention.

Manual slide clamp 66 may also be provided to control flow through tubing 44, being particularly used as an on-off control as the device is connected to water bag 49.

The above has been offered for illustrative purposes only, and is not intended to limit the invention of this application, which is as defined in the claims below.

That which is claimed is:

1. A humidifer for gases which comprises a metal can defining cylindrical walls and a closed bottom end, and a housing defining a well receiving said can in snug-fitting relationship, wick means positioned within said can for absorbing water in said can and presenting it in dispersed form to gases flowing through said can; a closure sealing the open mouth of said can, said closure defining gas inlet and outlet aperture ports communicating with the can interior; said closure also defining a light access port, and transparent probe means communicating with said light access port and extending into said can, said transparent probe means defining an end surface within the can interior which includes angled surfaces positioned to permit light passing in said transparent probe toward said end surface to be reflected again up the probe away from said end surface when said end surface is out of contact with liquid, and to be transmitted through said end surface when said probe is in contact with said liquid; photosensitive means positioned to detect reflected light in said probe, tubing communicating with the can interior through said closure at one end and adapted for communicating at its other end with a source of liquid; valve means for controlling liquid flow through said tubing; and transducer means for opening said valve means when said light sensing means detects reflected light in said transparent probe, and for closing said valve means when reflected light is not detected in said transparent probe, whereby gases passing into the gas inlet and out of the outlet are humidified by contact with liquid taken up by said wick means from a supply of liquid in said can having a volume controlled by the controlled amount of liquid flow through said tubing into the can.

2. The humidifier of claim 1 in which a partition separates said inlet and outlet ports and extends inwardly therebetween, to reduce shunting of gases between said inlet port and outlet port.

3. The humidifier of claim 1 in which said partition extends at least one-third of the length of said can.

4. A humidifier for gases which comprises a metal can defining cylindrical walls and a closed bottom end, and a heater housing defining a well receiving said can in snug-fitting relationship, a heating element adjacent said well for providing heat to liquid in said can by conduction through the can wall, to warm the liquid to improve the level of humidification of gases passing therethrough; wick means positioned within said can for absorbing water in said can and presenting it in dispersed form to gases flowing through said can; a closure sealing the open mouth of said can, said closure defining gas inlet and outlet aperture ports communicating with the can interior; said closure also defining a light access port, and transparent probe means communicating with said light access port and extending into said can to at least the remotest one-third of the can interior from said closure, said transparent probe means defining an end surface adjacent said remotest one-third of the can interior which includes angled surfaces positioned to permit light passing in said transparent probe toward said end surface to be reflected again up the probe away from said end surface when said end surface is out of contact with liquid, and to be transmitted through said end surface when said probe is in contact with said liquid; photosensitive means positioned to detect reflected light in said probe, flexible tubing communicating with the can interior through said closure at one end and adapted for communicating at its other end with a source of liquid at an elevated position over said can and closure; valve means for controlling liquid flow through said tubing; and transducer means for opening said valve means when said light sensing means detects reflected light in said transparent probe, and for closing said valve means when reflected light is not detected in said transparent probe, whereby gases passing into the gas inlet and out of the outlet are humidified by contact with liquid taken up by said wick means from a supply of liquid in said can of controlled volume of no more than one-third of the internal volume of the can.

5. The humidifier for gases of claim 4 in which said can is made of seamless metal and is of the shape and wall thickness of a commerical beverage can.

6. The humidifier for gases of claim 5 in which said metal can is made of aluminum.

7. The humidifier of claim 5 in which a partition separates said inlet and outlet ports and extends inwardly therebetween, to reduce shunting of gases between said inlet port and outlet port.

8. The humidifier of claim 7 in which said partition extends at least one third of the length of said can.

* * * * *